United States Patent [19]
Podney

[11] Patent Number: 5,293,119
[45] Date of Patent: Mar. 8, 1994

[54] ELECTROMAGNETIC MICROSCOPE FOR EVALUATION OF ELECTRICALLY CONDUCTIVE AND MAGNETIC MATERIALS

[75] Inventor: Walter N. Podney, San Diego, Calif.

[73] Assignee: SQM Technology, Inc., La Jolla, Calif.

[21] Appl. No.: 837,967

[22] Filed: Feb. 20, 1992

[51] Int. Cl.⁵ .................. G01N 27/87; G01R 33/035
[52] U.S. Cl. .................................. 324/242; 324/241; 324/248; 324/262; 505/842
[58] Field of Search ............... 324/248, 225, 226, 227, 324/234, 236, 238–243, 260–263, 229; 505/842–846

[56] References Cited
U.S. PATENT DOCUMENTS

| | | | |
|---|---|---|---|
| 3,764,897 | 10/1973 | Greenwood | 324/229 |
| 4,165,480 | 8/1979 | Morrison . | |
| 4,549,135 | 10/1985 | Vaidya . | |
| 4,613,816 | 9/1986 | Zeamer | 324/248 |
| 4,639,675 | 1/1987 | Hinton | 324/248 X |
| 4,855,677 | 8/1989 | Clark, Jr. et al. | 324/238 |
| 4,982,158 | 1/1991 | Nakata et al. . | |
| 5,004,724 | 4/1991 | De . | |
| 5,053,834 | 10/1991 | Simmonds . | |
| 5,059,903 | 10/1991 | Otaka et al. . | |

Primary Examiner—Kenneth A. Wieder
Assistant Examiner—Warren S. Edmonds
Attorney, Agent, or Firm—James Creighton Wray

[57] ABSTRACT

An instrument for non destructive evaluation (NDE) is called an electromagnetic microscope, formed by superconductive microprobes arrayed in parallel rows. When moved over a test piece, the array generates a scanned image of flaws, stress variations or changes in composition. Each microprobe has a drive coil a few mm in radius that encircles pickup loops forming a concentric, coplanar gradiometer 1 mm or less in diameter, coupled to a superconducting quantum interference device (SQUID). Drive coils transmit an oscillating magnetic field that induces eddy or magnetization currents in conductive or ferromagnetic materials, respectively. The gradiometer senses distortions in paths of induced currents. The sensitivity of SQUIDs increases sensitivity, penetration depth, and spatial resolution of flaws.

19 Claims, 4 Drawing Sheets

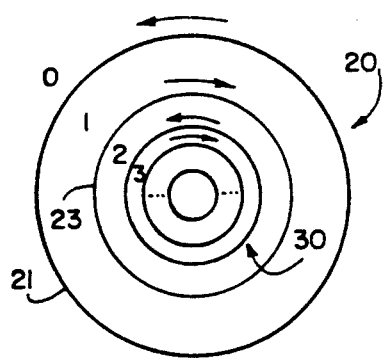
FIG. 1A
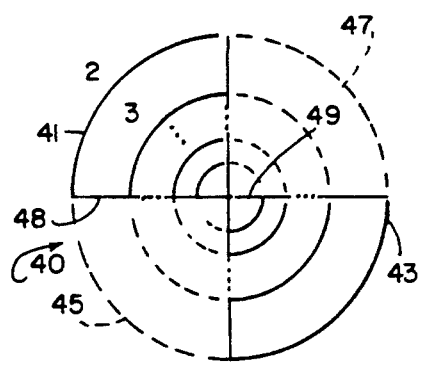
FIG. 1B
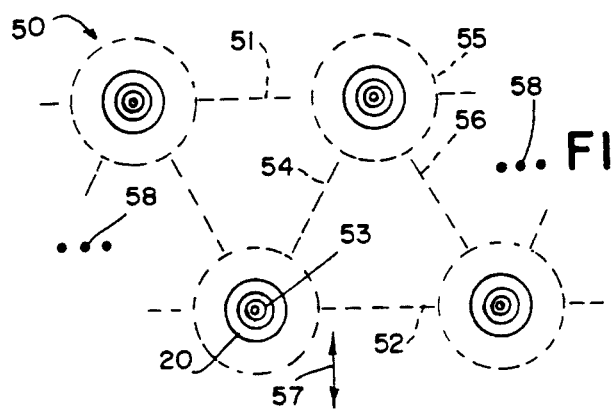
FIG. 2
FIG. 3
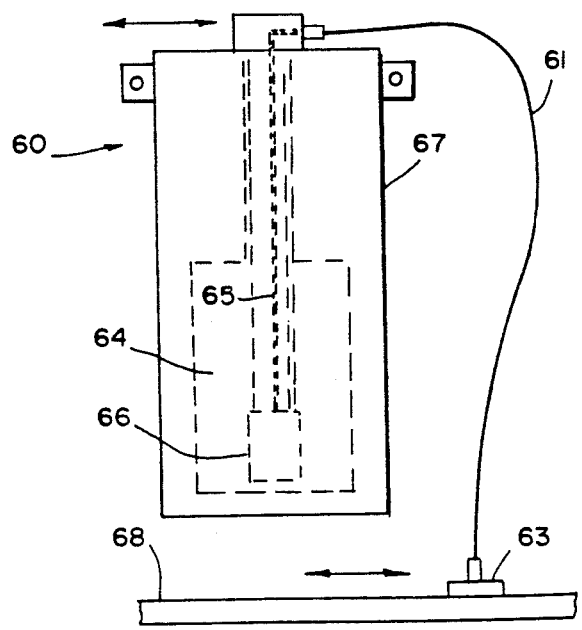

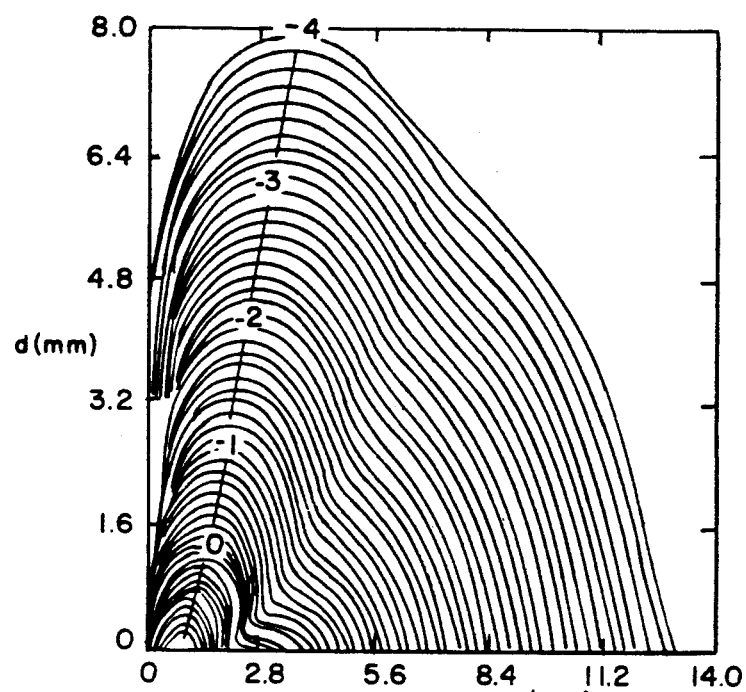
FIG. 4A
FIG. 4B
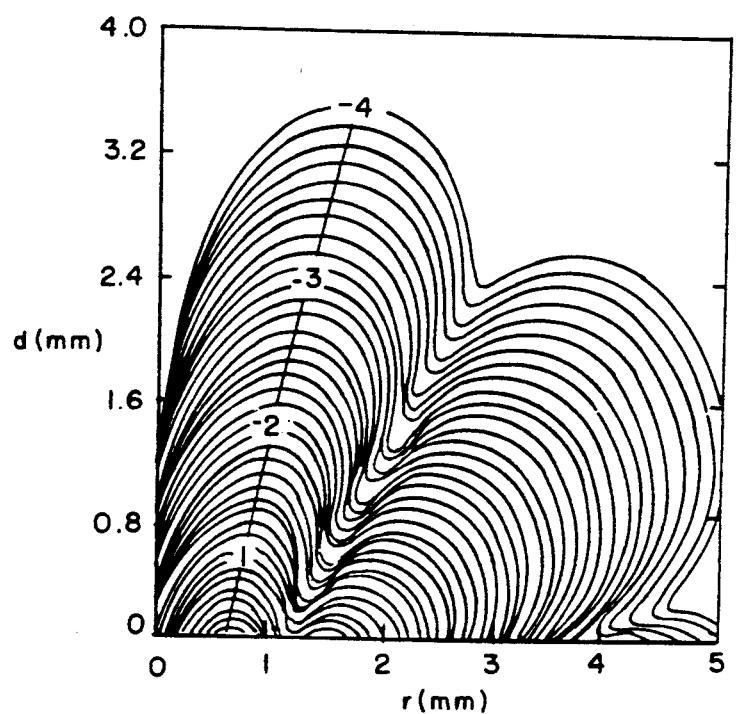

ELECTROMAGNETIC MICROSCOPE FOR EVALUATION OF ELECTRICALLY CONDUCTIVE AND MAGNETIC MATERIALS

BACKGROUND OF THE INVENTION

Eddy current and magnetic methods are two common techniques for non destructive evaluation (NDE) of materials and parts. Technology in present use seriously limits range of application, because existing sensors lack either sensitivity, bandwidth, spatial resolution, or combinations of these properties. For example, eddy current systems typically use induction coil receivers to detect the magnetic field of oscillating eddy currents induced in a metallic object. Because signal to noise varies linearly with frequency, they are constrained to operate at frequencies from tens of kHz to a few MHz. In a conductor, induced currents are exponentially attenuated with depth below the surface, according to the skin depth $\delta = \sqrt{1/\pi\mu_o\sigma f}$, where $\mu_o$ is the permeability of vacuum, $\sigma$ is the material's conductivity, and $f$ is the oscillation frequency. For aluminum alloys, $\delta \approx 1$ mm at 10 kHz. Conventional systems are insensitive to flaws buried deeper than one or two skin depths below the surface. Furthermore, induction coil receivers require a large turns-area product to attain adequate sensitivity, sacrificing spatial resolution in the process. They fail to meet simultaneously all three requirements of sensitivity, penetration depth, and resolution.

A need has long existed to provide improved sensitivity, penetration depth and spatial resolution in non destructive evaluation of flaws within conductors and magnetic materials.

SUMMARY OF THE INVENTION

An electromagnetic detector of the present invention provides significant improvements in sensitivity, penetration depth, and spatial resolution over the state of the art. Herein are described an instrument and results of analytical performance models applied to eddy current inspection for flaws in nonferrous, conductive materials. The invention provides detection of flaws 0.1 mm in radius at a depth of several mm in aluminum, with horizontal resolution of the order of 1 mm and a vertical resolution of about 0.3 mm.

An electromagnetic microscope of the invention has plural superconductive microprobes arrayed in parallel rows for moving over a test piece. The array generates a scanned image of flaws, stress variations, and changes in composition. Each microprobe has drive coils greater than 1 mm in radius. Inner pickup loops, forming a concentric, coplanar gradiometer 1 mm or less in diameter, are inductively coupled to a superconducting quantum interference device (SQUID). Drive coils transmit an oscillating magnetic field that induces eddy or magnetization currents in conductive or ferromagnetic materials, respectively. The gradiometer senses distortions in paths of induced currents. The sensitivity of SQUIDs increases sensitivity, penetration depth, and spatial resolution over existing eddy current and magnetic NDE systems.

An electromagnetic microscope apparatus has an array of microprobes. Each microprobe has one or more drive coils and pickup loops forming a concentric coplanar gradiometer preferably and a superconducting quantum interference device (SQUID) connected to the pickup loops.

A power source is connected to the drive coils for producing a changing magnetic field that induces eddy currents and magnetization currents in conductive and magnetic materials, respectively.

The pickup loops which form the gradiometer preferably are less than 1 mm in diameter.

In preferred embodiments, the pickup loops are arranged in opposite sectors on the gradiometer.

Preferably the microprobes are arranged in a pattern of equilateral triangles in a pair of parallel rows. Plural microprobes are arranged in a pair of parallel rows, with the microprobes arranged at points of equilateral triangles.

The centers of the plural microprobes are spaced apart four times the radial field of view.

Preferably plural microprobes are connected to plural SQUIDS.

The SQUIDS are mounted in a liquid helium bath within a vacuum jacket and the microprobes are connected to the SQUIDS by a flexible cryogenic umbilical cord, which includes electrical connectors for supplying current to the drive coils and communicating sensed currents from the pickup loops to the SQUIDS, and heat conductors for transferring heat and cooling the microprobes.

An electromagnetic microscope instrument of the invention senses flaws in a conductive or magnetic material. The instrument has a movable cryostat and a flexible umbilical cord having distal and proximal ends. The proximal end of the cord is attached to the cryostat, and a movable eye is connected to the distal end of the cord for moving on the material. A window is mounted on the eye for contacting the material. Microprobes are mounted in the eye, and the microprobes have drive coils and pickup loops forming a pattern of concentric coplanar gradiometers.

Each microprobe of an array of microprobes has drive coils and pickup loops which form a concentric coplanar gradiometer and superconducting quantum interference devices (SQUIDs) are connected to the pickup loops.

These and further and other objects and features of the invention are apparent in the disclosure, which includes the above and ongoing written specification, with the claims and the drawings.

BRIEF DESCRIPTION OF THE DRAWINGS

FIG. 1A shows a configuration of source coils and pickup loops that comprise a microprobe.

FIG. 1B shows receiver pickup loops forming a planar, biaxial gradiometer.

FIG. 2 represents a segment of an array of biaxial microprobes forming part of the eye of an electromagnetic microscope.

FIG. 3 illustrates elements of an electromagnetic microscope.

FIG. 4A shows contours of the response expected from a gradiometer of order two.

FIG. 4B shows contours of the response expected from a gradiometer of order four.

DETAILED DESCRIPTION OF THE DRAWINGS

Figure 6:
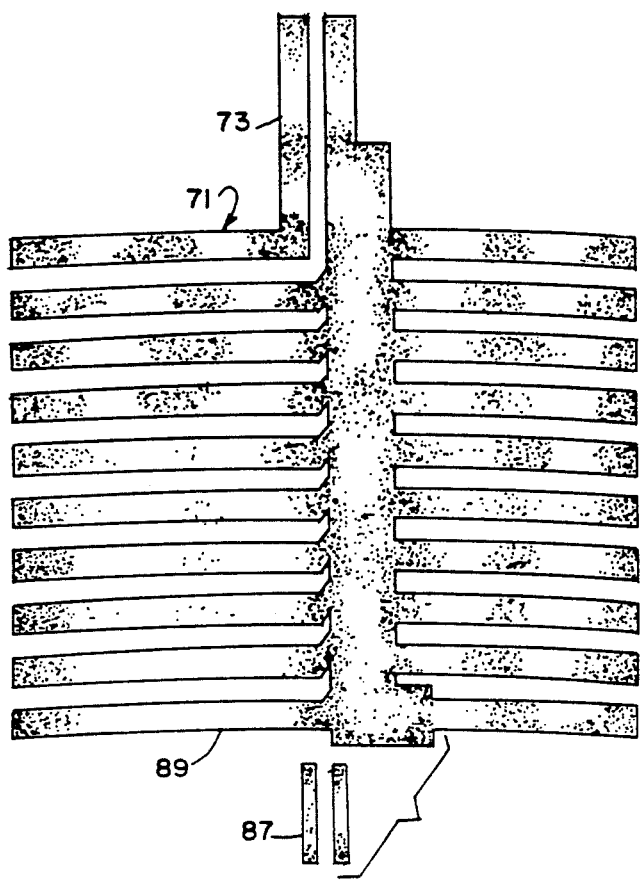
FIG. 6 schematically shows an enlarged fragment detail of the loop leads and drive coil.

FIG. 1A shows a configuration of source coils 0, 1 and pickup loops 2, 3 . . . 2+n that comprise a microprobe 20. The source coils and pickup loops form a coplanar nest of concentric circles. The two outermost coils 21 and 23 carry an oscillating electric current to drive eddy currents. Current in the inner drive coil 1 opposes current in the outer coil 0 to suppress interference from the source at the receiver 30, formed by the innermost loops 2, 3 . . . 2+n. Loops of the receiver 30 wind oppositely to form a planar gradiometer of order n, where n is the number of loops. FIG. 1B shows receiver windings divided into pairs of opposing quadrants to form a biaxial gradiometer of order n for resolving heading to a flaw.

In FIG. 1A, a coplanar nest of drive coils 0, 1 and pickup loops 2, 3 . . . 2+n form a planar gradiometer of order n. The two outermost loops, numbered 0 and 1, are drive coils that carry a changing current to excite eddy currents. Their currents flow oppositely, as marked by arrows, to null interference from drive currents at the receiver, formed by n innermost loops, numbered 2 through 2+n. Arrows show that they wind oppositely. Triple dots, . . . , between receiver loops denote continuation of windings to loop n+2.

In another preferred embodiment, pickups are arranged coaxially. Other pickup configurations are within the scope of this invention.

In FIG. 1B, receiver pickup loops 2, 3 . . . 2+n−1, 2+n form a planar, biaxial gradiometer 40 of order n. Opposite quadrants 41, 43 form pickup loops of an axis, as marked by heavy lines. Dashed lines mark pickup loops 45, 47 of the second axis. Adjacent loops wind oppositely as shown by arrows. Closures 48 for each loop run parallel along diameters, and crossovers 49 are at the center. Triple dots, . . . , between loops denote continuation of windings to loop n+2.

The relations $$\sum_{i=1}^{n} N_i(r_i)^{m+1} = 0, \text{ for } m = 1, 2, 3, \ldots, n-1, \quad (1)$$

specify ratios of radii, $r_i$, and number of turns, $N_i$, of the n concentric loops of a receiver. The constraints expressed by Equation 1 result by rejecting gradients up to order n of the net flux threading the receiver from a dipole on the axis of the loops.

For a gradiometer of second order, the constraint is $N_2 r_2^2 = -1$, for $r_1 = 1$ and $N_1 = 1$. The number of turns is positive for a right handed winding and negative for a left handed winding. The response of a second order gradiometer to a dipole at position z on the axis is proportional to $z^{-5}$, to lowest order. For a gradiometer of third order, response to a dipole on the axis is again proportional to $z^{-5}$, to lowest order, because the response to a dipole contains even powers of r alone. For a gradiometer of fourth order, the response is proportional to $z^{-7}$, to lowest order. For $N_1 = 1$ and $r_1 = 1$ and $N_2 = -2$, $N_3 = 2$, and $N_4 = -2$, the constraint for a gra-diometer of fourth order requires $r_2 = 0.899$, $r_3 = 0.635$, and $r_4 = 0.308$.

Current, $I_1$, in the inner coil 1 of the source balances current in its outer coil, $I_o$, so net flux from the source vanishes at the receiver. The current is set so that $I_1 = -\beta I_o$, where $\ominus$ is a balance factor. The balance factor $\beta$ depends on mutual inductances, $M_{ij}(h)$, between source loops 0 and 1 and receiver loops 2 through m+2, as expressed by the relation $$\beta = \frac{M_{02}(h) + M_{03}(h) + \ldots + M_{0n}}{M_{12}(h) + M_{13}(h) + \ldots + M_{1n}}, \quad (2a)$$

with n=m+2. The expression $$M_{ij}(h) = M_{ij}^{00} + \quad (2b)$$

$$\mu_0 \pi N_i r_i N_j r_j \int_0^\infty \frac{(1-\gamma/k)}{(1+\gamma/k)} e^{-2kh} J_1(kr_i) J_1(kr_j) dk$$

gives the mutual inductance between coplanar, concentric loops of radii $r_i$ and $r_j$ at height h above an electrically conducting plate, where $\gamma^2 = k^2 + i\mu_0 \sigma \omega$, $\sigma$ is electrical conductivity of the plate, $\omega$ is the carrier frequency, $\mu_0 = 4\pi \times 10^{-7}$ H/m, and $J_1(X)$ is a Bessel function of the first kind and order one. Here, the expression $$M_{ij}^{00} = \mu_0 N_i N_j [(r_i^2 + r_j^2) K(\rho_{ij}^0) - (r_i + r_j)^2 E(\rho_{ij}^0)] \quad (2c)$$

gives mutual inductances far above the plate (h>>0) and/or at low frequency ($\gamma \approx k$), where the exponential term in Equation 2b vanishes. Functions $K(\rho)$ and $E(\rho)$ are complete elliptic integrals of the first and second kinds, respectively, and $$\rho_{ij}^0 = 2\sqrt{r_i r_j} /(r_i + r_j).$$

The number of turns and radius, $N_1$ and $r_1$, of the inner drive coil are chosen so that $\beta$ is unity far above the plate. Near the plate, amplitude and phase of the factor $\beta$ specify current in the inner drive coil needed to null interference.

An array 50 of microprobes 20 forming the "eye" of an electromagnetic microscope comprises pairs of parallel rows 51, 52, as shown in FIG. 2. Each receiver axis 53 is coupled to a SQUID. Spacing between microprobe centers is four times the radial field of view, which is the greatest radial distance at which a flaw of given size and depth can be detected. The two rows form a pattern of equilateral triangles 54. Scanning in a direction 57 perpendicular to the rows gives complete coverage. The arrangement is both the smallest spacing without overlap and the widest spacing that ensures complete coverage.

FIG. 2 shows a segment of an array 50 of biaxial microprobes 20 forming part of the eye of an electromagnetic microscope. Dashed circles 55 mark the radial field of view for each microprobe 20. Dashed lines 56 connecting centers highlight the equilateral, triangular pattern 54. The arrow 57 shows the direction of scan, and dots 58 denote continuing replication of the array 50.

FIG. 3 is a schematic representation of a complete instrument 60. A flexible, cryogenic umbilical cord 61 about 1 m long thermally grounds the eye 63 of the microscope to a bath 64 of liquid helium. Leads 65 couple the gradiometer loops to SQUIDs 66 in the cryostat 67. The eye is housed behind a thin window within one mm or so of the test surface. The radiant heat leak through the window, about 7 μW/(mm)², is small enough that a single microprobe can be cooled to about 5K using a copper wire 1 mm in radius inside a superinsulated, flexible, stainless steel vacuum jacket. Large arrays may require either a cryogenic heat pipe or continuous cooling using liquid helium.

FIG. 3 shows elements of an electromagnetic microscope. The sensing eye 63 moves above a test plate 68. A flexible, cryogenic umbilical cord 61 connects the eye 63 to SQUIDs 66 immersed in liquid He inside a remote cryostat 67. The cryostat 67 moves to stay within reach of the eye 63 as it scans the plate 68.

Analysis of the response expected from a flaw gives performance of an electromagnetic microprobe for eddy current evaluation of conductive materials. Current oscillating in a circular loop parallel to the surface of a uniformly conducting half-space induces eddy currents that flow in concentric circles about the axis of the source loop. A flaw acts as a small, spherical void that perturbs the circular flow. For a deep flaw that is far from boundaries and much smaller than a skin depth, the induced current is effectively uniform over its dimensions. Current flow diverted by a flaw is the sum of the uniform flow and flow from a current dipole at the center of the void. The dipole moment $\vec{M}$ is given in terms of the flaw volume V and unperturbed eddy current density $\vec{J}_s$ as $$\vec{M} = -(3/2) V \vec{J}_s. \quad (3)$$

The dipole opposes the induced current to null current within the void. For an irregular flaw, the diverted or scattered current includes multipole terms of higher order.

Reciprocity allows expressing the flux threading a receiver loop, $\phi_r$, from a flaw in terms of vector potentials by the relation $$\frac{\phi_r}{I_s} = \frac{3}{2} Vi\omega\sigma \left[\frac{\vec{A}_s \cdot \vec{A}_r}{I_s I_r}\right], \quad (4a)$$

where $\vec{A}_s$ and $\vec{A}_r$ are vector potentials produced at a flaw by currents $I_s$ and $I_r$ in source and receiver loops, respectively. Here, the expression $$A_i(r,d) = \mu_0 N_i I_i r_i Y_i(r,d) \quad , \quad (4b)$$

where $$Y_i(r, d) = \int_0^\infty \left[\frac{e^{-\gamma d - kh}}{\gamma/k + 1}\right] J_1(kr_i) J_1(kr) dk, \quad (4c)$$

and $\hat{\phi}$ is an azimuthal unit vector, gives the vector potential, $A_i(r,d)$, at a flaw at radius r and depth d, of a current, $I_i$, oscillating at a frequency $\omega$ in a loop with $N_i$ turns of radius $r_i$ at height h above a material of conductivity $\sigma$.

Equation 4a, giving the flux threading a receiver loop from a flaw, then says that the expression $$G_n(r,d) = \mu_0 \frac{3}{2} Vi\mu_0\sigma\omega I_0 [N_0 r_0 Y_0(r,d) - \beta N_1 r_1 Y_1(r,d)] \times \quad (5)$$

$$\sum_{i=2}^{n+2} N_i r_i Y_i(r,d)$$

gives the response of a microprobe, $G_n(r,d)$, with a receiver forming a gradiometer of order n, to a flaw at depth d and radial distance r from the center of the probe. It is the net flux threading the receiver for current $I_o$ in the outermost coil of two balanced source coils. The function $Y_i(r,d)$ measures sensitivity of a loop to a flaw at depth d and radial distance r.

Equation 5 for the response of a microprobe describes the response of microprobes of orders two and four. A microprobe of odd order (2n+1) gives the same response as one of one order lower (2n), because the response to a dipole contains even powers of r alone. A spherical flaw 0.1 mm in radius is at depth d in an aluminum plate and at radial distance r from the center of the microprobe. The microprobe carries a current of 1A in the main drive coil, oscillating at a frequency of 1 kHz, and sits 1 mm above the surface. Skin depth in aluminum is 2.68 mm at a frequency of 1 kHz Tables 1 and 2 give coil specifications for microprobes of second and fourth order, respectively. Source coils are numbers 0 and 1; receiver loops are numbers 2 through 5.

TABLE 1

| Microprobe of Second Order | | | | |
|---|---|---|---|---|
| i | 0 | 1 | 2 | 3 |
| $N_i$ | 16 | −4 | 1 | −4 |
| $r_i$, mm | 3 | 2 | 1 | 0.5 |

TABLE 2

| Microprobe of Fourth Order | | | | | | |
|---|---|---|---|---|---|---|
| i | 0 | 1 | 2 | 3 | 4 | 5 |
| $N_i$ | 16 | −4 | 1 | −2 | 2 | −2 |
| $r_i$, mm | 3 | 2 | 1 | 0.90 | 0.64 | 0.31 |

FIG. 4A shows contours of constant magnitude of the complex response of a microprobe of second order in the r,d plane for flaw depths to 8 mm and radii out to 14 mm. Contours range from a magnitude of 10 $\phi_o$/A to $10^{-4}$ $\phi_o$/A. A flux quantum, $\phi_o$, is $2.07 \times 10^{-15}$ Tm². They show that peak response exceeds SQUID sensitivity out to radii of 13 mm or so and depths to 8 mm, for a drive current of 1A. The line cutting across contours traces migration of peak response with flaw depth. It is a measure of horizontal resolution of a microprobe.

FIG. 4B shows contours of constant magnitude of the complex response of a microprobe of fourth order in the r,d plane for flaw depths to 4 mm and radii out to 5 mm. Contours range from a magnitude of 0.5 $\phi_o$/A to $10^{-4}$ $\phi_o$/A. They show that peak response exceeds SQUID sensitivity out to radii of about 5 mm and depths to 3.5 mm, for a drive current of 1A. Again, the line crossing contours traces migration of peak response with flaw depth.

Depth of field is taken as the depth at which the peak signal from a flaw falls below $10^{-4}$ $\phi_o/\sqrt{HZ}$, which is the sensitivity of a SQUID sensor. Depth of field depends on flaw size, gradiometer order, and frequency and amplitude of the source current. It is proportional to flaw volume and to amplitude of the source current.

FIGS. 4A and 4B show that depth of field is about 8 mm, for a gradiometer of second order, and is about 3.5 mm, for a gradiometer of fourth order, to a flaw 0.1 mm in radius at an operating frequency of 1kHz with a source current of 1A. A second order gradiometer gives more than a twofold advantage in depth of field.

Field of view is taken as the maximum radius at which the signal from a flaw falls below $10^{-4}\phi_o/\sqrt{HZ}$, for a flaw at a fixed depth. It depends on flaw size, gradiometer order, and frequency and amplitude of the drive current, as does depth of field. Contours at $10^{-4}$ $\phi_o/A$ in FIGS. 4A and 4B trace field of view to a 0.1 mm flaw as a function of flaw depth, for second and fourth order gradiometers, respectively, operating at a frequency of 1 kHz with a drive current of 1A.

For a gradiometer of second order, field of view is about 3 mm for a flaw at the depth of field of about 8 mm. It increases to nearly 13 mm for flaws near the surface. For a gradiometer of fourth order, field of view is about 1.5 mm for a flaw at the depth of field of about 3.4 mm.

The locus of peak magnitude in FIGS. 4A and 4B gives a linear change in resolution with flaw depth, for gradiometer of second and fourth orders respectively. For second order, we find that the relation $$r_p = 0.371\, d + 0.792 \tag{6a}$$

gives the radius of the contour marking the peak magnitude, $r_p$, for a flaw depth d, both measured in millimeters. Radius increases linearly from 0.792 mm for a surface flaw to 3.76 mm at the depth of field of 8 mm. For fourth order, the relation $$r_p = 0.256\, d + 0.65 \tag{6b}$$

gives the contour radius. It increases linearly from 0.65 mm for a surface flaw to 1.55 mm at the depth of field of 3.52 mm.

Spacing of contours in FIGS. 4A and 4B give a measure of vertical resolution. Differences between contours represent a 26% change in drive current amplitude. Near the depth of field, a 26% change in current amplitude gives a change in depth of field of 0.24 mm for a second order gradiometer and 0.133 mm for a fourth order gradiometer. A vertical resolution of a few tenths of a millimeter is produced for a 0.1 mm flaw.

High performance microprobes form the magnetic eye of an electromagnetic microscope for high revolution, wide field of view, and large depth of field for imaging internal flaws in aluminum and residual stress in steel plates. A cryogenic umbilical connects the eye to a remote cryostat housing SQUID sensors to provide ease of scanning and to make the electromagnetic microscope a versatile tool. Drive coils a few millimeters in radius together with coplanar receiver loops 1 mm or less in radius form a high performance microprobe. Current in the drive coils oscillates at frequencies from a few Hz, for evaluation of ferrous materials, to a few kHz, for evaluation of nonferrous, conductive materials.

Figure 5:
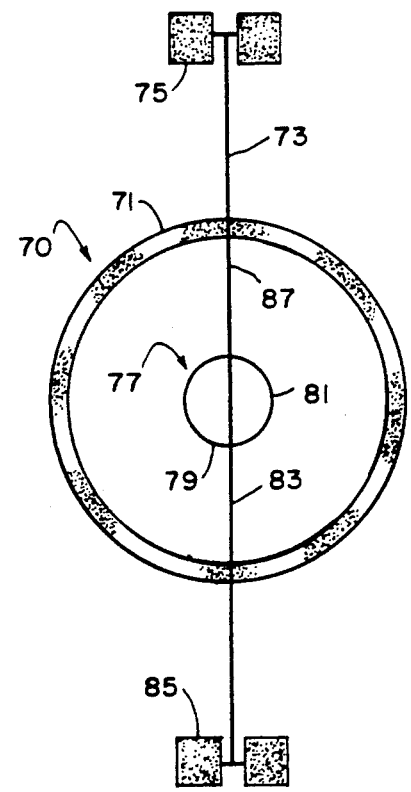
FIG. 5 shows a preferred printed circuit microprobe having a printed drive coil, pickup loop leads and connector pads for use in an eye of the electromagnetic microscope.

A preferred embodiment of a printed circuit microprobe 70 is schematically shown in FIG. 5. A drive coil 71 and a pickup 77 are formed as thin layer printed circuits. Ends of a large drive coil 71 are connected through leads 73 to drive coil connection pads 75. A smaller gradiometer pickup 77 is made of semicircular loops 79 and 81 which are connected through leads 83 to pickup loop connection pads 85.

Leads 73 are connected to opposite ends of drive coil 71 to supply current through the coil. Leads 87 are dummy leads for symmetry in the printed circuit. Ends of parallel leads 87 are open.

Leads 73, 83 and 87 are parallel. The closely spaced leads 73 and 83 are connected individually to connection pads 75 and 85. Loop sections 79 and 81 to sense current in pickup 77.

FIG. 6 is an enlarged fragment detail of leads 73 and drive coil 71, which is formed in a spiral 89 of from 10 to about 40 turns. The sloped areas connecting the turns are insulated from the extended lead 73 on the right. Dummy leads 87 appear at the bottom.

Figure 7:
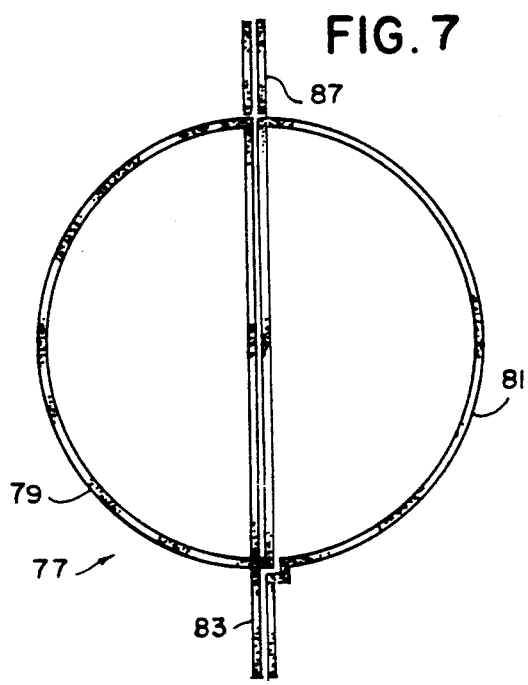
FIG. 7 is an enlarged view of the pickup loop and the leads.

FIG. 7 is a detail of pickup 77. The straight central portion of loop 79 extends directly upward from the left lead 83. The straight central portion of loop 81 extends directly upward from the lower end of loop 79. Loop 81 connects at its lower end to the right lead 83.

Figure 8:
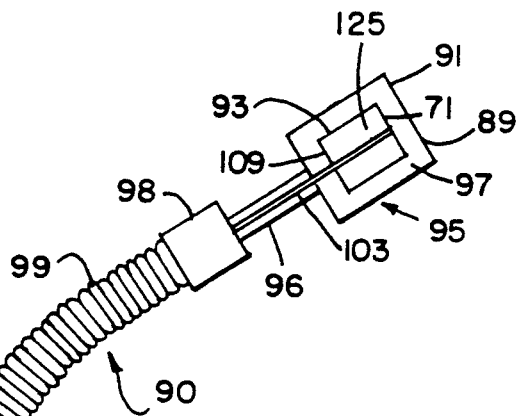
FIG. 8 shows a perspective of the microprobes mounted on an end of a heat-conducting silicon cylinder and attached to a storage container.
Figure 9:
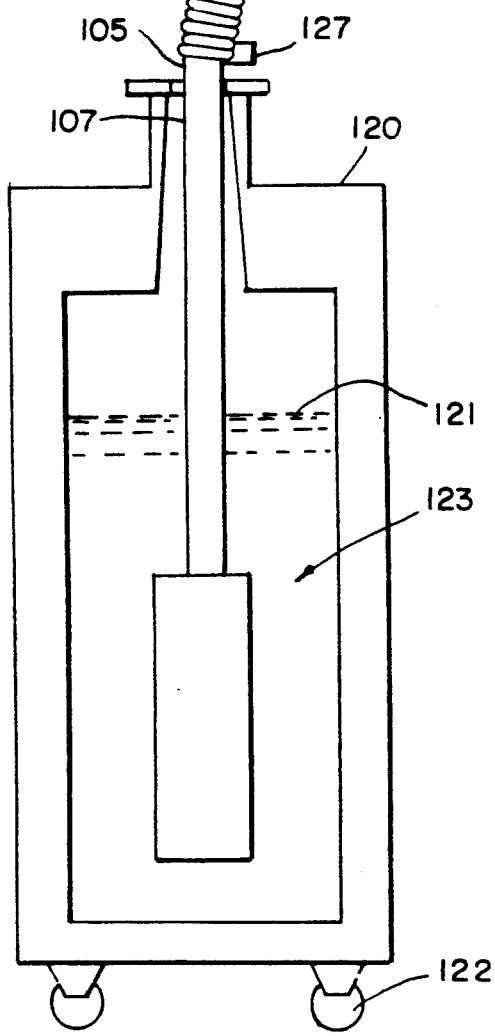
FIG. 9 shows an enlarged, detailed section of the wire spiral barrel springs in the vacuum chamber.
Figure 9:
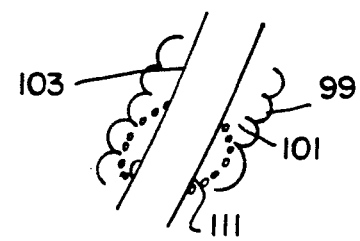

As shown in FIGS. 8 and 9, several printed circuit microprobes 71 are spaced from a thin sapphire window 91 in a fiberglass shell 95 at the end of umbilical cord 90. The microprobes 71 are mounted on an end of a heat-conducting pure silicon cylinder 93. The window is sealed to the end of a fiberglass shell 95 which forms a vacuum chamber 97 around the cylinder 93. A stainless steel tube 96 extends from an expansion joint 98 at the end of a stainless steel bellows shell 99 and forms a vacuum chamber 101 around a braided copper wire heat transfer sheath 103. A proximal end 105 of bellows 99 is connected to a stainless steel tube 107. The proximal end of the sheath extends to the bottom of tube 107 and its distal end is connected to a copper plate 109, which is attached to an end of the silicon cylinder 93. Thin wire spiral barrel springs 111 with large centers and small ends space the stainless steel bellows 99 from the flexible copper wire sheath 103.

A storage container 120 for liquid helium 121 is mounted on wheels 122.

The stainless steel tube 107 and the flexible copper sheath 103 extend into the liquid helium, where the SQUIDs are housed in a cluster of three niobium tubes 123. Niobium-titanium connecting wires 125 extend along and through the silicon cylinder 93 from contact pads 75 and 85 on each gradiometer and extend through the sheath 103 in the umbilical cord 90 to the SQUIDs 123. The vacuum chamber 101 is evacuated through fitting 127.

In one embodiment a standard commercial container 120 for liquid helium is employed. The stainless steel tube is about ¾ inch diameter by 2 feet long. The flexible bellows is about ¾ inch in diameter and about 3 to 9 feet long. The copper sheath is about ½ inch in diameter and is made of about 1200 strands of 36 gauge copper wire. The barrel-shaped spacer coil springs have about a ¼ inch diameter at ends and a larger diameter in the middle, and are spaced at about 14 inch intervals. The silicon cylinder is about 1 inch in diameter and 1 inch long. The fiberglass shell is about 1/16 inch thick and about 1½ inches in diameter. The liquid helium is held at about 4.2°K and the temperature of the printed circuit gradiometers is about 5°K.

The invention may be used in the form of telescopes with large drive coils and large pickup loops connected to SQUIDs in movable cryogenic containers, for example in checking pipelines for latent faults.

While the invention has been described with reference to specific embodiments, modifications and variations of the invention may be constructed without departing from the scope of the invention, which is defined in the following claims.

What is claimed is:

1. An electromagnetic flaw detecting apparatus, comprising an array of probes, each probe having a pickup loop forming a gradiometer and a drive coil, and a superconducting quantum interference device (SQUID) connected to the pickup loops, wherein plural SQUIDS are mounted in a liquid helium bath within a vacuum jacket and plural probes are connected to the SQUIDS by a flexible cryogenic umbilical cord, which includes electrical connectors for supplying current to the drive coils and for communicating sensed currents from the pickup loops to the SQUIDS, and thermal conductors for cooling the plural probes.

2. The apparatus of claim 1, further comprising the pickup loop forming a concentric coplanar configuration.

3. The apparatus of claim 1, further comprising a power source connected to the drive coils of the probes for producing a changing magnetic field that induces eddy currents and magnetization is electrically conductive and magnetic materials, respectively.

4. The apparatus of claim 1, wherein the probes are microprobes and the pickup loops forming the gradiometers are less than about 2 mm in diameter.

5. The apparatus of claim 1, wherein the pickup loops are arranged in opposite sectors on the gradiometer.

6. The apparatus of claim 1, wherein the probes are arranged in a pattern at apexes of equilateral triangles.

7. The apparatus of claim 1, wherein plural probes are arranged in a pair of parallel rows, with the probes arranged at points of equilateral triangles.

8. The apparatus of claim 1, wherein the coils and pickups are formed as printed circuits with printed leads and connector pads.

9. An electromagnetic microscope instrument for sensing flaws in a conductive or magnetic material, comprising a moveable cryostat, a flexible umbilical cord having distal and proximal ends, the proximal end of the cord being attached to the cryostat, a movable eye connected to the distal end of the cord for moving on the material, a window mounted on the eye for contacting the material, microprobes mounted in the eye within the window, the microprobes having pickup loops forming gradiometers, drive coils, and sensors connected to the pickup loops.

10. The instrument of claim 9, the sensors further comprising a superconducting quantum interference device (SQUID) connected to each pickup loop.

11. The instrument of claim 9, wherein the microprobes further comprise an array, each microprobe having a pickup loop forming a gradiometer and a drive coil, and a superconducting quantum interference device (SQUID) positioned in the cryostat and connected to the pickup loop.

12. The instrument of claim 9, wherein the pickup loops forming the gradiometers are less than about 1 mm in diameter.

13. The instrument of claim 9, wherein the pickup loops are arranged in opposite sectors on the gradiometer.

14. The instrument of claim 9, wherein the microprobes are arranged in a pattern at apexes of equilateral triangles.

15. The instrument of claim 9, wherein the microprobes are formed as printed circuits having the coils and the pickups.

16. The instrument of claim 15, wherein the pickups are constructed as opposed semicircular loops with straight central portions and curved outer portions.

17. The instrument of claim 9, wherein the umbilical cord comprises an outer bellows enclosing a vacuum chamber and a flexible heat conductive sheath having proximal and distal ends, and wherein the eye comprises a thin window, a shell connected to the window and to the outer bellows and forming a vacuum chamber extension in the eye, wherein the microprobes comprise printed circuit gradiometers.

18. The instrument of claim 17, wherein plural SQUIDS are mounted in a liquid helium bath in the cryostat and the plural microprobes are connected to the SQUIDS by the flexible umbilical cord, which includes electrical connectors for supplying current to the drive coils and communicating sensed currents from the pickup loops to the SQUIDS, and thermal conductors within a vacuum jacket for cooling the plural microprobes.

19. The method of detecting flaws, comprising positioning a probe on a material to be tested, creating changing magnetic fields with an array of drive coils in the probe, sensing currents in an array of pickup loops in the probe, communicating the sensed currents through electrical connectors in a thermally insulated, flexible umbilical cord to SQUIDS within a liquid helium bath, cooling the pickup loops from the bath via the umbilical cord, moving the probe on the material, sensing changes in the currents in the electrical connectors with the SQUIDS, and thereby sensing flaws in the material.

* * * * *